US012551632B2

(12) United States Patent
Orr et al.

(10) Patent No.: US 12,551,632 B2
(45) Date of Patent: Feb. 17, 2026

(54) HOLDER FOR SYRINGES AND OTHER MEDICAL INSTRUMENTS

(71) Applicant: KoDa Ideaworks, LLC, Waunakee, WI (US)

(72) Inventors: Karen Denise Orr, Madison, WI (US); Douglas Randolph Arnold, Waunakee, WI (US)

(73) Assignee: KODA Ideaworks, Inc., Waunakee, WI (US)

( * ) Notice: Subject to any disclaimer, the term of this patent is extended or adjusted under 35 U.S.C. 154(b) by 934 days.

(21) Appl. No.: 17/734,203

(22) Filed: May 2, 2022

(65) Prior Publication Data

US 2023/0347069 A1 Nov. 2, 2023

(51) Int. Cl.
*A61M 5/32* (2006.01)

(52) U.S. Cl.
CPC ... *A61M 5/3204* (2013.01); *A61M 2205/0288* (2013.01); *A61M 2205/586* (2013.01)

(58) Field of Classification Search
CPC ................ A61M 5/3204; A61M 5/008; A61M 2205/0288; A61M 2205/586; A61B 2050/3002; A61B 50/20
See application file for complete search history.

(56) References Cited

U.S. PATENT DOCUMENTS 3,696,920 A * 10/1972 Lahay .................... A61B 50/30 206/370
3,727,658 A * 4/1973 Eldridge, Jr. ......... H01F 7/0215 206/370
4,232,784 A * 11/1980 Hesselgren ............ A61C 19/02 206/370
4,380,292 A 4/1983 Cramer
(Continued)

FOREIGN PATENT DOCUMENTS

BR 11201224392-6 A2 5/2016
EP 0510626 A1 4/1992
(Continued)

OTHER PUBLICATIONS

2017 Aspen Surgical Product Catalog, p. 37, Syringe Holders.
(Continued)

*Primary Examiner* — Stanton L Krycinski
(74) *Attorney, Agent, or Firm* — Craig Fieschko; DeWitt LLP

(57) ABSTRACT

A medical instrument holder includes a base block configured to removably mount to a placement surface, and has prongs extending therefrom. A receiving block formed of soft and resiliently flexible material, such as an elastomeric foam, may be impaled on the prongs. A medical instrument (such as a syringe or scalpel) may be inserted into the receiving block, thereby effectively removably holding the medical instrument with respect to the placement surface. The receiving block may be discarded after use, and
(Continued)

replaced with another receiving block for subsequent use. The holder is particularly useful for receiving the cap of a hypodermic syringe within the receiving block, allowing the syringe to be held in a ready-to-use location, and allowing one-handed removal of the syringe from the cap grasped by the receiving block.

20 Claims, 3 Drawing Sheets

(56) References Cited

U.S. PATENT DOCUMENTS

| | | | | | |
|---|---|---|---|---|---|
| 4,599,314 | A * | 7/1986 | Shami | C12M 23/12 | 294/160 |
| 4,846,803 | A | 7/1989 | Emerson | | |
| 4,936,449 | A * | 6/1990 | Conard | A61B 50/362 | 206/382 |
| 4,938,354 | A | 7/1990 | Hernandez | | |
| 4,986,817 | A | 1/1991 | Code | | |
| 5,005,710 | A * | 4/1991 | Hofer | B25H 3/04 | D6/567 |
| 5,046,624 | A * | 9/1991 | Murphy | A61B 50/20 | D24/227 |
| 5,078,695 | A | 1/1992 | Farrar, Jr. et al. | | |
| 5,129,886 | A * | 7/1992 | Sincock | A61M 5/008 | 604/263 |
| 5,265,724 | A * | 11/1993 | Dondlinger | B09B 3/0075 | 220/8 |
| 5,279,577 | A * | 1/1994 | Collett | A61M 5/3213 | 248/176.1 |
| 5,311,985 | A * | 5/1994 | Suida | A61M 5/3213 | 206/210 |
| 5,334,151 | A * | 8/1994 | Santilli | A61M 5/3213 | 206/365 |
| 5,348,543 | A | 9/1994 | Talley | | |
| 5,372,252 | A * | 12/1994 | Alexander | A61B 50/39 | 206/370 |
| 5,399,169 | A * | 3/1995 | Stein | A61M 5/3213 | 206/365 |
| 5,797,885 | A | 8/1998 | Rubin | | |
| 5,850,917 | A * | 12/1998 | Denton | A61M 5/3278 | 206/370 |
| 5,967,778 | A * | 10/1999 | Riitano | A61C 19/002 | 433/102 |
| 5,975,295 | A * | 11/1999 | Diamond | A61M 5/008 | 206/366 |
| 6,279,743 | B1 * | 8/2001 | Ballard | A61M 5/3204 | 211/70.6 |
| 6,540,072 | B1 * | 4/2003 | Fischer | B05C 17/00593 | 604/218 |
| D474,274 | S * | 5/2003 | Walters | D24/227 | |
| 6,877,984 | B2 * | 4/2005 | Tinnin | A61C 19/002 | 433/102 |
| 6,971,879 | B2 * | 12/2005 | Discko, Jr. | A61C 19/006 | 433/163 |
| 7,066,329 | B2 * | 6/2006 | Riley | A61B 50/30 | 206/370 |
| 7,837,034 | B2 * | 11/2010 | Clegg | A61M 5/008 | 206/370 |
| 7,913,841 | B2 | 3/2011 | Clegg et al. | | |
| 7,975,846 | B2 | 7/2011 | Clegg et al. | | |
| 8,511,468 | B2 * | 8/2013 | Reeves | A61B 50/20 | 248/176.1 |
| 9,452,025 | B2 * | 9/2016 | Allen | A61B 50/33 | |
| 10,864,316 | B2 * | 12/2020 | Fraites | A61M 5/008 | |
| 11,266,791 | B2 * | 3/2022 | Bonomo | A61M 5/3204 | |
| 11,771,844 | B2 * | 10/2023 | Yeary | A61M 5/3204 | 206/571 |
| 2009/0005794 | A1 * | 1/2009 | Lowry | A61B 17/06061 | 606/148 |
| 2013/0012887 | A1 | 1/2013 | Giuberchio | | |
| 2022/0249784 | A1 * | 8/2022 | Morse | A61M 5/3204 | |

FOREIGN PATENT DOCUMENTS

| | | | | |
|---|---|---|---|---|
| FR | 2664816 | A1 | 7/1990 | |
| GB | 2486232 | A * | 6/2012 | A61B 50/33 |
| JP | 2020258859 | A | 4/2020 | |
| WO | WO 199302871 | A1 | 10/1993 | |
| WO | WO 2007/065110 | A2 | 6/2007 | |
| WO | WO 2007/065110 | A3 | 6/2007 | |

OTHER PUBLICATIONS

Aspen Surgical Scalpel-Syringe Holder, https://www.aspensurgical.com/catalog.patient-staff-safety/miscellaneous-safety-accessories/foam-scalpel-holder/112001ptx, captured Mar. 25, 2022.
2016 Qosina Catalog, p. 319, Syringe Holders.
Qosina Saf-T Cube Needle Holder, https://www.scientistlive.com/content/25390, captured Mar. 28, 2022.
Qosina Single Syringe Handling Block, https://www.qosina.com/single-syringe-handling-block.31333#gref, captured Feb. 18, 2022.
European Patent Office, International Search Report for PCT/US2023/018845, Jul. 6, 2023.
Japanese Patent Office, May 29, 2025 Office Action for parallel Japanese appln. JP2024-256.
Brazilian Patent Office, Jun. 10, 2025 Office Action for parallel Brazilian appln. BR112024020704.

* cited by examiner

HOLDER FOR SYRINGES AND OTHER MEDICAL INSTRUMENTS

FIELD OF THE INVENTION

This document concerns an invention relating generally to holders for medical instruments, particularly for hypodermic syringes, and more specifically to instrument holders which can grasp and retain instruments such as hypodermic syringes with use of a single hand.

BACKGROUND OF THE INVENTION

In the medical field, it is often necessary to retain instruments ready at hand for use, while at the same time guarding against potential injury from, or contamination to, such instruments. As an example, syringe holders have been developed which hold a syringe in a ready-to-use position by grasping its syringe cap, which covers the syringe's needle when the syringe is not in use to maintain sterility and avoid accidental needle punctures. These holders allow a user to pull the syringe from the cap to expose the needle for use, and then replace the needle within the grasped cap to mount the syringe for later use if needed. Examples are seen in prior patents such as U.S. Pat. No. 4,846,803 to Emerson; U.S. Pat. No. 4,938,354 to Hernandez; U.S. Pat. No. 4,986,817 to Code; U.S. Pat. No. 5,078,695 to Farrar, Jr. et al.; U.S. Pat. No. 5,797,885 to Rubin; U.S. Pat. No. 7,975,846 to Clegg et al.; WO199302871 to Collett; EP0510626 to Herotec Kunststoffverarbeitung; and FR2664816 to Cabinet Ores. Other examples are the flexible foam syringe/scalpel holders offered by Aspen Surgical (Caledonia, MI, USA) and Quosina Corporation (Ronkonkoma, NY, USA). The Aspen holder is a rectangular prism (e.g., a cube-like block) formed of flexible foam bearing double-sided tape on its bottom, whereby a backing sheet could be removed from the tape and the prism could then be adhered to a surgical drape. The cap of a syringe could then be inserted into a small-diameter hole formed in the prism's top, or could simply be urged into the foam to penetrate the prism, with the foam's elasticity then tending to retain the inserted cap. The syringe could then be pulled from the cap retained within the mounted prism for use, with the syringe's needle being reinsertable within the cap when use is completed. Quosina provided similar holders, as well as providing a retainer in the form of a small plastic open-topped box having double-sided tape on its base. The retainer could be adhered to a surface, and a foam prism could be inserted into the open top of the retainer for use similar to the aforementioned Aspen holder.

The Aspen and Quosina holders are relatively low-cost items which may be discarded after use, avoiding the need for sterilization, and may be inexpensively replaced with a new holder for subsequent use. However, the foam prisms, once adhered to surgical drapes, are not always stable, with the double-sided tape sometimes failing to adhere well to the fabric of the drapes, and/or with the drapes bending/folding to allow the prisms (and any syringes therein) to tip. While the prisms could instead be adhered to surgical trays or other surfaces, this tends to leave adhesive residue on the surfaces, requiring additional post-operation cleaning. Additionally, the prisms hold instruments such that the instruments protrude vertically from the tops of the prisms, leaving elongated instruments (such as syringes) vulnerable to accidental strikes (and dislodgement from prisms) during operations.

SUMMARY OF THE INVENTION

The invention involves an instrument holder which is intended to at least partially solve the aforementioned problems. To give the reader a basic understanding of some of the advantageous features of the invention, following is a brief summary of preferred versions of the instrument holder, with reference being made to the accompanying drawings (which are briefly reviewed in the following "Brief Description of the Drawings" section of this document) to assist the reader's understanding. Since the following discussion is merely a summary, it should be understood that more details regarding the preferred versions may be found in the Detailed Description set forth elsewhere in this document. The claims set forth at the end of this document then define the various versions of the invention in which exclusive rights are secured.

Looking to the exemplary preferred version of the invention depicted in FIGS. 1*a*-1*b*, the instrument holder 100 includes a rigid and durable base block 10 having elongated prongs 10*p*, and a receiving block 20 formed of soft pierceable material, allowing it to be impaled on the prongs 10*p* (as depicted in FIGS. 3*b*-3*c*). The instrument holder 100 further includes mounting means for removably and inviolably mounting the base block 10 to a placement surface 200 such as a tray or tabletop in an operating room. (The term "inviolable mounting" refers to attachment which does not damage the placement surface 200 or otherwise leave any noticeable adhesive or other residue on the placement surface 200, i.e., the placement surface 200 is in essentially the same state after removal of the base block 10 as it was prior to the mounting of the base block 10.) Here the mounting means is provided by a mounting block 30 which is magnetically attracted to the base block 10 (or to which the base block 10 is magnetically attracted). The mounting block 30 allows mounting of the base block 10 to the placement surface 200 in the manner shown in FIGS. 3*a*-3*b*, wherein the mounting block 30 is situated on the opposite side of the placement surface 200 from the base block 10 such that the base and mounting blocks 10 and 30 are magnetically bound to each other about the placement surface 200. With the base block 10 so affixed to the placement surface 200, an instrument can pierce the receiving block 20 to be held ready for use. This is illustrated in FIGS. 3*d*-3*f*, where the cap 300*c* for a hypodermic syringe 300 penetrates the receiving block 20 (FIG. 3*e*). The syringe 300 is then withdrawn from the cap 300*c* (FIG. 3*f*), allowing the user to unsheath the needle 300*n* of the syringe 300 with a single hand, and leaving the cap 300*c* readily available to resheath the needle 300*n* (and hold the syringe 300 as in FIG. 3*e*) when use of the syringe 300 is completed. The receiving block 20 can be removed from the base block 10 and discarded after a single use, or alternatively can undergo multiple uses before being removed and discarded, with a new receiving block 20 being installed on the base block 10 for subsequent use.

The prongs 10*p* preferably extend from an upper base block surface 10*u*, and preferably have lengthwise axes which are at least approximately parallel. The prongs 10*p* are preferably situated adjacent the side base block surfaces 10*s*, with each prong 10*p* being situated closer to an edge of the upper base block surface 10*u* than to any other prong 10*p*, such that when the receiving block 20 is centrally penetrated by an instrument (see, e.g., FIGS. 3*d*-*f*), the prongs 10*p* are unlikely to obstruct penetration (i.e., an instrument will not experience interference from a prong 10*p* within the receiving block 20). The opposing lower base block surface $\mathbf{10}_L$ can then bear the aforementioned mounting means, which (as shown in FIG. 2) can take the form of a magnet or ferromagnetic material 10*m* on or within the lower base block surface $\mathbf{10}_L$ (with the mounting block 30 then bearing cooperative magnetic or ferromagnetic material 30*m*). Alternatively, the mounting means might take the form of one or more suction cups (as exemplified by FIG. 4*a*) or a tacky surface (e.g., a silicone or other tacky gel pad, as exemplified by FIG. 4*b*) on the lower base block surface $10_L$, allowing the base block 10 to be removably and inviolably mounted to the placement surface 200 without the use of a mounting block 30.

The receiving block 20 is preferably formed of resiliently expandable material, that is, the material can deform to accommodate prongs 10*p* and instruments 300 penetrating the receiving block 20, but tends to attempt to return to its original unpenetrated form, thereby grasping any penetrating prongs 10*p*/instruments 300 (such grasping being defeatable by a user with minimal effort when pulling the receiving block 20 from the prongs 10*p*, or pulling an instrument from the receiving block 20). As discussed in greater detail below, resiliently flexible polymeric foams are a preferred material for the receiving block 20. As best seen in FIG. 1B, the receiving block lower surface 20L may have prong apertures 20*p* preformed therein to ease penetration by the prongs 10*p* of the base block 10, with such prong apertures 20*p* being formed with smaller diameters than the prongs 10*p* so that the prong apertures 20*p* can expand about the prongs 10*p* during insertion. One or more of the receiving block side surfaces 20*s*, and/or its receiving block upper surface 20*u*, may likewise have one or more instrument apertures 20*i* preformed therein. Such prong and/or instrument apertures 20*p* and 20*i* are preferably defined by, or are otherwise situated at, the intersection of valleys 20*v* formed within the receiving block 20 (these valleys 20*v* preferably being simple cuts/slits formed in the receiving block 20, with the cuts/slits of the valleys 20*v* of FIGS. 1*a*-1*b* extending entirely through the receiving block 20 to open at opposing sides of the receiving block 20). Such valleys 20*v* better accommodate larger instruments (e.g., larger-diameter veterinary hypodermic syringes 300), as well as better accommodating inexact (off-center) insertion of prongs 10*p*/instruments 300.

The mounting block 30 (if provided) includes an upper mounting block surface 30*u* which is magnetically attracted to the lower base block surface $10_L$, a lower mounting block surface 30L, and side mounting block surfaces 30*s* therebetween. A handle 30*h* may be provided on the lower mounting block surface 30L (as in the exemplary instrument holder 100 shown in the drawings) or on a side mounting block surface 30*s*, allowing the mounting block 30 to be more easily pulled from a placement surface 200 towards which the mounting block 30 is magnetically attracted (via the base block 10 on the opposing side of the placement surface 200).

Further potential advantages, features, and objectives of the invention will be apparent from the remainder of this document in conjunction with the associated drawings.

BRIEF DESCRIPTION OF THE DRAWINGS

FIGS. 1*a*-1*b* (collectively referred to as FIG. 1) depict an exemplary instrument holder 100, wherein:

FIG. 1*a* depicts the instrument holder 100 in its typical orientation when in use, but in exploded (disassembled) form, with the mounting block 30 being ready to (magnetically) affix the base block 10 to a placement surface (not shown) situated between the base block 10 and the mounting block 30, and with the receiving block 20 being shown ready to install on the prongs 10*p* of the base block 10.

FIG. 1*b* depicts the instrument holder 100 inverted from the orientation of FIG. 1*a*, such that the opposite sides of the receiving block 20, base block 10, and mounting block 30 of FIG. 1*a* are shown.

FIGS. 3*a*-3*f* (collectively referred to as FIG. 3) illustrate an exemplary use of the instrument holder 100 of FIGS. 1-2, wherein:

FIG. 3*a* depicts the base block 10 atop a placement surface 200 (e.g., a tray in an operating room), with the mounting block 30 ready for installation on the opposite side of the base block 10 via magnetic attraction to the base block 10.

FIG. 3*b* depicts the receiving block 20 ready for installation on the base block 10 by impaling it on the prongs 10*p* of the base block 10.

FIG. 3*c* depicts the receiving block 20 as installed on the base block 10.

FIG. 3*d* depicts a capped hypodermic syringe 300 ready for installation in the receiving block 20 by inserting the cap 300*c* within the instrument aperture 20*i* of the receiving block 20.

FIG. 3*e* depicts the withdrawal of the hypodermic syringe 300 from the cap 300*c*, thereby readying the syringe 300 for use.

FIG. 3*f* depicts the hypodermic syringe 300 after removal from its cap 300*c* within the receiving block 20, and ready for reinstallation within the cap 300*c*.

FIGS. 4*a*-4*b* (collectively referred to as FIG. 4) illustrate a base block modified from that of FIGS. 1-3, wherein:

FIG. 4*a* depicts the base block 10 of the foregoing Figures modified to bear a suction cup 10*c* for mounting the base block 10 to a placement surface.

FIG. 4*b* depicts the base block 10 of the foregoing Figures modified to bear a tacky gel pad 10*g* for mounting the base block 10 to a placement surface.

DETAILED DESCRIPTION OF EXEMPLARY VERSIONS OF THE INVENTION

Figure 1A:
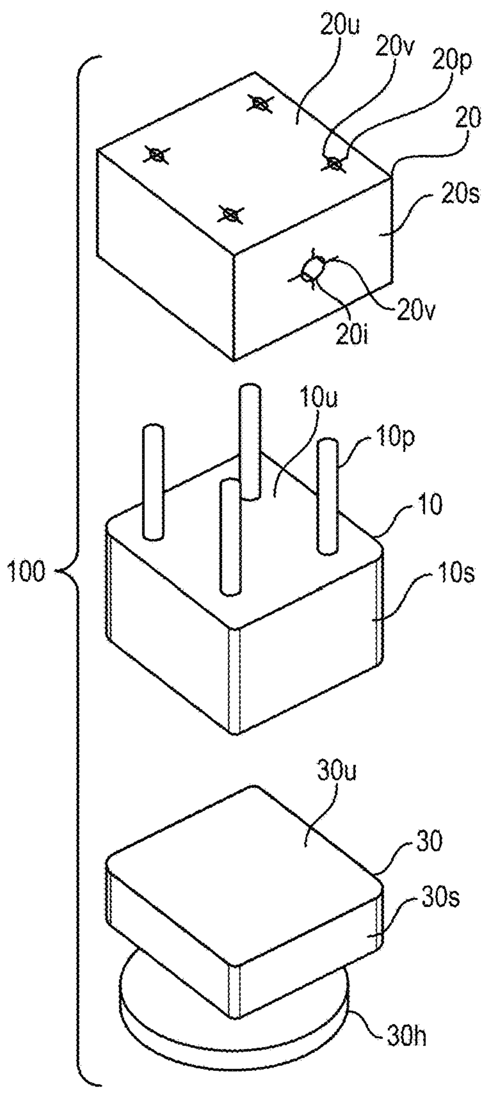
Figure 1B:
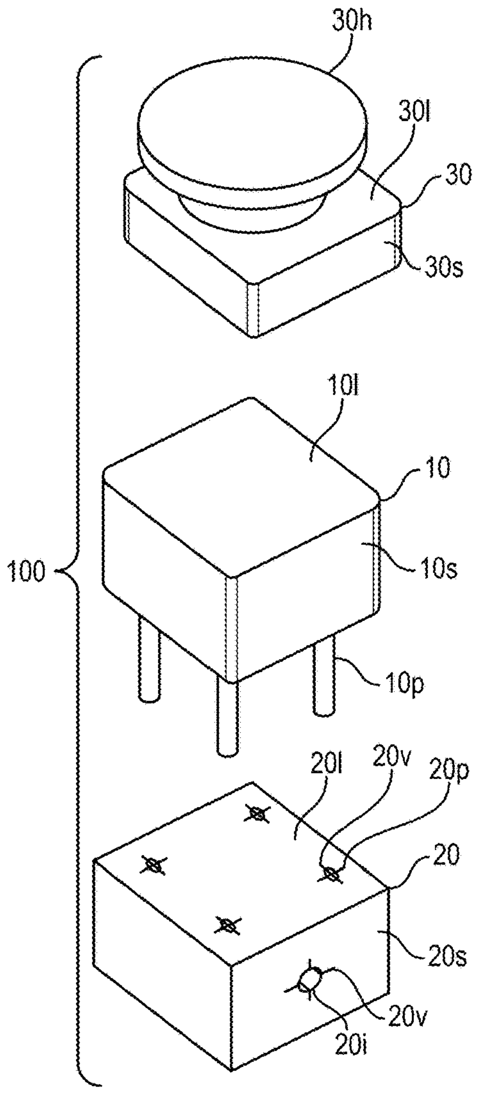

Expanding on the discussion above, the receiving block 20 may have any shape suitable for receiving the instrument(s) it is intended to receive. (More generally, throughout this document, term "block" refers to a body having any shape. Thus, for example, the receiving block need not take the shape of a rectangular prism, and could have a dome-like or other shape.) The material of the receiving block 20 is preferably resiliently expandable, that is, it can deform to accommodate instruments penetrating the receiving block 20, but tends to attempt to return to its original unpenetrated form, thereby grasping any penetrating instrument. Where no apertures are formed in receiving block 20, it is also preferably made of material which is sufficiently soft that it can be pierced by an instrument urged into the receiving block 20. Exemplary materials for the receiving block 20 include closed-cell or open-cell foams made of ethylene-vinyl acetate (EVA), polyethylene, polyurethane, polyester, polyether, or vinyl nitrile. Natural or synthetic sponge, or soft solid materials such as silicone rubber, paraffin, or other soft polymeric materials, could alternatively be used.

As depicted in the Figures, the instrument aperture 20*i* extends entirely through the depth of the receiving block 20 from one of the side receiving block surfaces 20*s* to the opposite side receiving block surface 20*s*, and has valleys 20*v* extending radially outwardly from the perimeter of the instrument aperture 20*i*, with these valleys 20*v* likewise extending entirely through the full depth of the receiving block 20. The prong apertures 20*p*, which are arrayed in the receiving block at locations allowing them to receive the prongs 10*p* of the base block 10, similarly extend entirely through the thickness of the receiving block 20 from the upper receiving block surface 20*u* to the lower receiving block surface 20L, and each has radially-extending valleys 20*v* extending entirely through the thickness of the receiving block 20. The valleys 20*v* depicted in the Figures are formed of cuts/slits in the receiving block 20 having negligible width between the sides of the valleys 20*v*, but may be formed with greater width (but preferably less than the diameter of any instrument/prong 10*p* to be inserted within the corresponding aperture). The valleys 20*v* beneficially allow easier insertion and removal of instruments/prongs 10*p* that have diameters greater than those of the apertures, and additionally better accommodate the insertion of instruments/prongs 10*p* which are not precisely centered with the apertures, with the valleys 20*v* tending to urge the inserted instruments/prongs 10*p* toward their apertures 20*i* and 20*p*.

In alternative versions of the receiving block 20, the apertures 20*i* and/or 20*p* and/or valleys 20*v* need not extend entirely through the receiving block 20. Additionally, apertures 20*i* and/or 20*p* might be provided in different numbers, and/or with different placement (e.g., one or more instrument apertures 20*i* might be provided on all of the side receiving block surfaces 20*s*, and/or on the upper receiving block surface 20*u*). Apertures 20*i* and/or 20*p* need not be provided with valleys 20*v*, or apertures 20*i* and/or 20*p* can simply be defined by the intersections of valleys 20*v*. The apertures 20*i* and/or 20*p* need not be defined as circular holes, and need not be provided at all where the prongs 10*p* and/or instruments 300 are simply to be urged into a surface of the receiving block 20 (in which case the prongs 10*p* and/or instruments 300 will form the apertures 20*i* and/or 20*p* as the prongs 10*p* and/or instruments 300 penetrate the receiving block 20).

The base block 10 and its prongs 10*p*, unlike the resiliently compressible (and expandable) receiving block 20, is preferably rigid and formed of durable materials which can be readily sterilized, such as metal (e.g., stainless steel) or hard plastic, or a combination thereof (e.g., a plastic base block 10 with protruding metal prongs 10*p*). Each prong 10*p* preferably has a width-to-depth ratio of approximately one (the width and depth being measured along axes perpendicular to the lengthwise axis of the prong 10*p*), and/or circularity (isoperimetric quotient) of approximately one, with a blunt tip to deter injury in the event that a user's hand/arm accidentally contacts the tip. Each prong 10*p* preferably has a length/height of at least one-third the height of the receiving block 20, such that the prongs 10*p* extend at least one-third of the way through a receiving block 20 impaled thereon, though lesser lengths can be used so long as the prongs 10*p* securely retain the receiving block 20 during use. While the prongs 10*p* may have lengths/heights greater than a receiving block 20 to be impaled thereon, such that the prongs 10*p* protrude from the receiving block upper surface 20*u* after installation of the receiving block 20 on the prongs 20*p*, it is preferred that the prongs 10*p* have a length/height no greater than the height of the receiving block 20.

Greater or fewer prongs 10*p* can be provided on the base block 10. Only a single prong 10*p* might be provided on the base block 10, but in this case the single prong 10*p* preferably has a width-to-depth ratio greater than one, or circularity (isoperimetric quotient) less than one, as a single prong 10*p* having a more circular cross-section is more susceptible to allowing the receiving block 20 to rotate about the prong 10*p* during usage. Thus, for example, a single prong 10*p* might be formed as a flange/plate, or with a trefoil or cruciform cross-section. Multiple sets of prongs 10*p* might be provided on a base block 10, with each set being provided to receive its own receiving block 20, whereby the base block 10 can accommodate multiple receiving blocks 20.

The prongs 10*p* preferably extend from the upper base block surface 10*u*, though they could alternatively or additionally be provided on one or more side base block surfaces 10. Regardless of the surface(s) of the base block 10 on which prongs 10*p* are provided, any receiving block(s) 20 to be received on the prongs 10*p* preferably has its instrument aperture 20*i*(s) oriented at least approximately perpendicular to the prongs 10*p* on which the receiving block 20 is to be impaled, thereby better avoiding later dislodgement of the receiving block 20 from the prongs 10*p* during removal and/or insertion of the instrument. The arrangement shown in the Figures, wherein the instrument aperture 20*i* is oriented parallel to the lower base block surface $\mathbf{10}_L$ (and thus to the placement surface 200 on which the base block 10 is to be mounted), beneficially also orients any inserted instrument parallel to the placement surface 200, leaving the instrument less susceptible to inadvertent collisions from a user's arm during operations (as can occur where an instrument extends more vertically from the receiving block 20).

Figure 2:
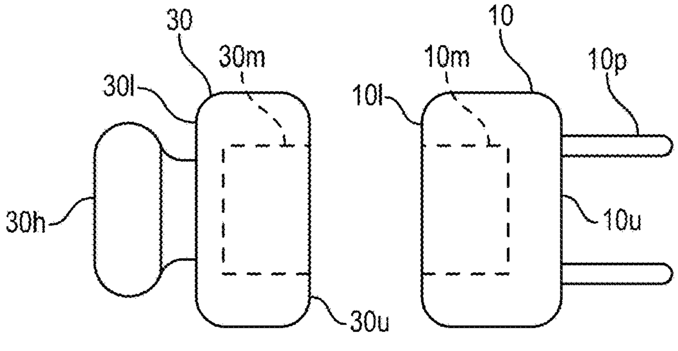
FIG. 2 shows a side view of the base block 10 and mounting block 30 of FIGS. 1*a*-1*b*, with the phantom (dashed) lines depicting the possible locations for magnets 10*m* and 30*m* in the blocks 10 and 30, or for a magnet in one block and ferromagnetic material in the other block, to provide magnetic attraction between the base block 10 and mounting block 30.
Figure 3A:
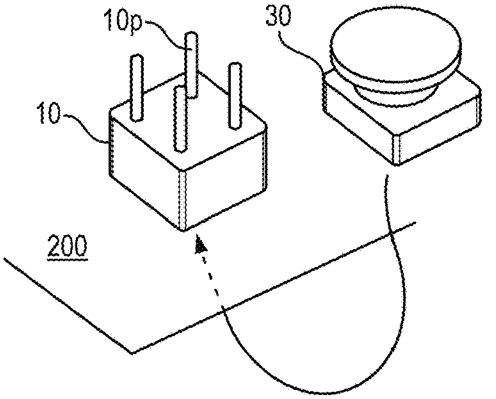
Figure 3B:
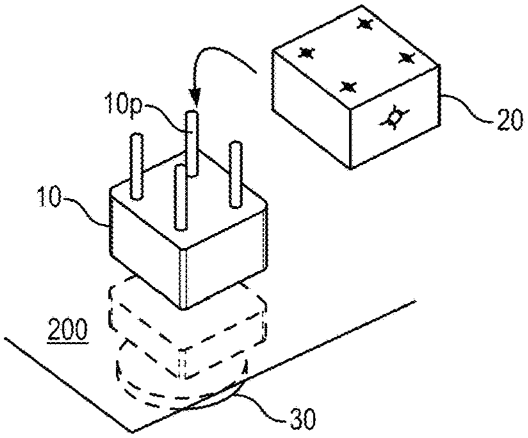
Figure 3C:
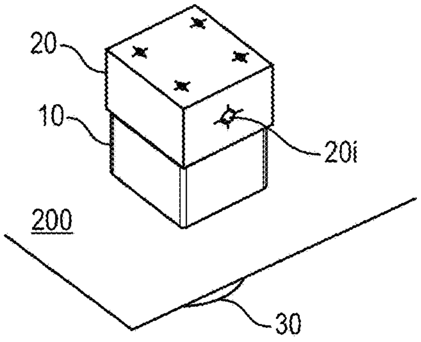
Figure 3D:
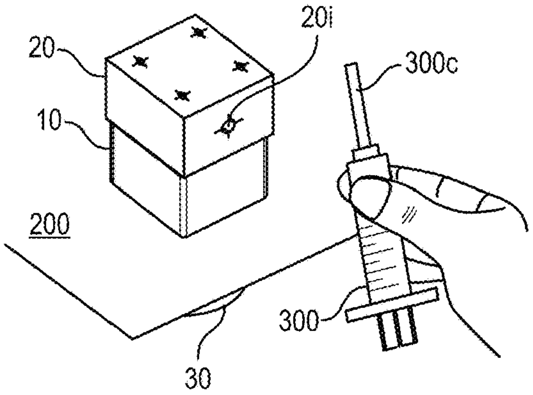
Figure 3E:
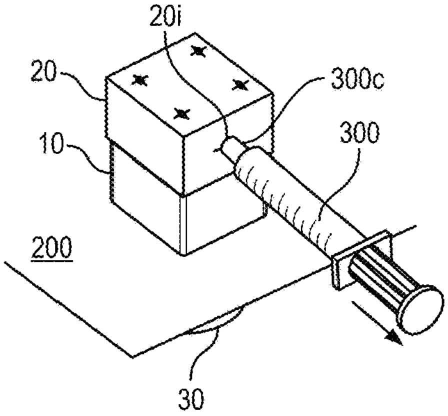
Figure 3F:
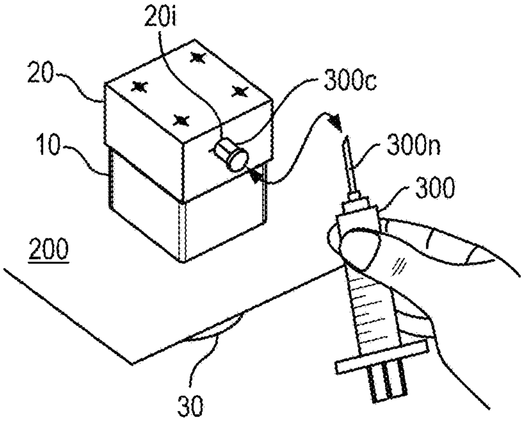
Figure 4A:
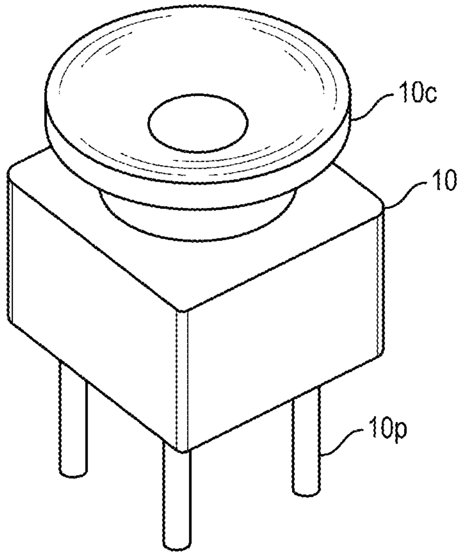
Figure 4B:
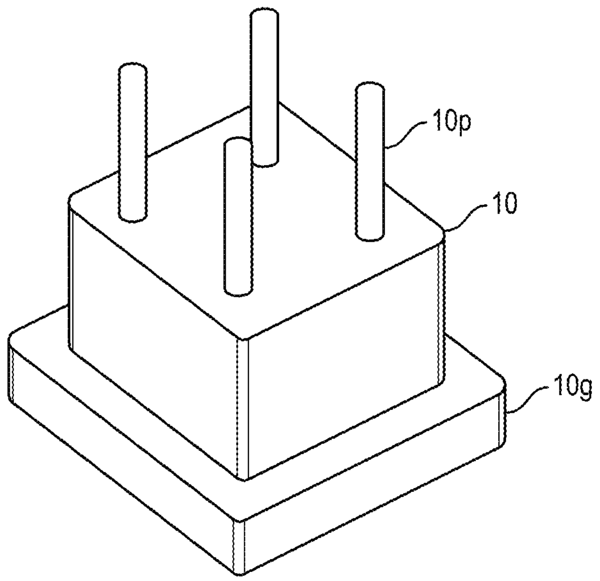

As noted previously, the base block 10 includes mounting means for removably and inviolably mounting to a placement surface 200, such as any one or more of a magnet (as at 10*m* in FIG. 2), a suction cup (as at 10*c* in FIG. 4*a*), or a tacky surface (e.g., a silicone or other tacky gel pad, as at 10*g* in FIG. 4*b*) on or within the lower base block surface $\mathbf{10}_L$. While those structures are preferred mounting means, alternatives are possible, such as a clip, clamp, or other mechanism which closes about the edge of a placement surface 200, or by providing the base block 10 with sufficient mass, and/or sufficient area at the lower base block surface $\mathbf{10}_L$, that it is effectively immovable during conventional use after placement on the placement surface 200. As examples, the base block 10 might have a mass of at least 2 kg, and/or might bear a plate at its lower base block surface $\mathbf{10}_L$ which extends outwardly from the side base block surfaces 10*s* by 10 cm or more (with the lower base block surface $\mathbf{10}_L$ possibly bearing elastomeric or other non-slip pads). Where the base block 10 is to use magnetic mounting means, a magnet—preferably a strong magnet such as a rare earth magnet—can be provided on or within the base block 10 (e.g., as an insert into the lower base block surface $\mathbf{10}_L$, as seen at 10*m* in FIG. 2) for attraction to a mounting block 30 containing a magnet 30*m* of opposite polarity, or otherwise containing ferromagnetic material (i.e., material which is attracted to a magnet). Conversely, the mounting block 30 could bear a magnet on or therein, with the base block 10 containing ferromagnetic material. Where the placement surface 200 is ferromagnetic, a magnetic base block 10 could simply be directly affixed to the placement surface 200 without the use of a mounting block 30. Alternatively, where a placement surface 200 is not ferromagnetic, a ferromagnetic plate could be adhered to the placement surface 200 to allow attraction of the magnetic base block 10 to the placement surface 200.

The mounting block 30, if provided, is (like the base block 10) preferably formed of rigid, durable, and sterilizable materials. The mounting block 30 preferably includes a handle 30*h* thereon, allowing it to be more readily grasped by a user's hand and pulled from a placement surface 200. While the depicted handle 30*h* takes the form of a knob protruding from the lower mounting block surface 30L, the handle 30*h* may alternatively or additionally be situated on a side mounting block surface 30*s*, and may take alternative forms such as one or more protruding loops or elongated members, or protrusions (e.g., ridges) or depressions (e.g., grooves) defined on one or more side mounting block surfaces 30*s*.

The invention encompasses the arrangement of the mounting block and receiving block described herein, as well as the receiving block alone (e.g., when sold as a consumable/disposable item for use with a separately-provided base block), and additionally the base block alone (e.g., when sold as a durable item for use with separately-provided consumable/disposable receiving blocks).

Throughout this document, various terms referring to orientation and position—e.g., "upper" (as in "upper receiving block surface") and "lower" (as in "lower receiving block surface")—should be regarded as relative terms rather than absolute ones. In other words, it should be understood (for example) that the upper receiving block surface being referred to may in fact be located at the side or bottom of the holder depending on the overall orientation of the holder. Thus, such terms should be regarded as words of convenience, rather than limiting terms.

Throughout this document, where a measurement or other value is qualified by the term "approximately," "about," "nearly," "roughly," or the like, this can be regarded as referring to a variation of 10% from the noted value. Thus, as an example, "approximately perpendicular" and "approximately parallel" can respectively be understood to mean within 9 degrees (i.e., 10% of 90 degrees) from perpendicular and parallel.

The invention is not intended to be limited to the preferred versions of the invention described above, but rather is intended to be limited only by the claims set out below. Thus, the invention encompasses all different versions that fall literally or equivalently within the scope of these claims. No term(s) expressed within any claim is to be construed in accordance with 35 U.S.C. 112(f) unless the words "means for" or "step for" are explicitly used in the terminology in question.

What is claimed is:

1. An instrument holder including:
- a. a base block having one or more elongated prongs extending therefrom, the base block being configured to removably and inviolably mount to a placement surface,
- b. a receiving block formed of material which is:
  - (1) resiliently expandable, and
  - (2) configured to be readily penetrated by the prongs when the receiving block is urged onto the prongs, with the receiving block thereby being removably affixed to the base block,
- c. a mounting block wherein:
  - (1) one of the base block and the mounting block contains magnetic material, and
  - (2) the other of the base block and the mounting block contains ferromagnetic material.

2. The instrument holder of claim 1 wherein the base block includes a lower base block surface having one or more of:
- a. a magnet therein or thereon,
- b. ferromagnetic material therein or thereon,
- b. a suction cup thereon, and
- c. a tacky surface thereon, configuring the base block to removably and inviolably mount to the placement surface.

3. The instrument holder of claim 2 wherein the prongs extend from an upper base block surface on the base block.

4. The instrument holder of claim 1 wherein the mounting block includes a handle thereon.

5. The instrument holder of claim 1 wherein:
- a. the base block has at least two of the prongs extending from a first surface thereon,
- b. the prongs have lengthwise axes which are at least approximately parallel,
- C. each prong is situated closer to an edge of the first surface than to any other prong.

6. The instrument holder of claim 1 wherein:
- a. the base block includes:
  - (1) an upper base block surface having the prongs extending therefrom,
  - (2) an opposing lower base block surface configured to removably and inviolably mount to a surface,
  - (3) a height extending between the upper and lower base block surfaces,
  - (4) a width extending orthogonal to the height,
  - (5) a depth extending orthogonal to the height and the width,
- b. the ratio of the width to the depth is approximately one, and
- c. the ratio of:
  - (1) the height to the width, and
  - (2) the height to the depth, is less than one.

7. The instrument holder of claim 1 wherein the receiving block includes:
- a. a first receiving block surface including at least one prong aperture formed therein, each prong aperture corresponding to a respective one of the prongs, and
- b. a second receiving block surface including an instrument aperture formed therein.

8. The instrument holder of claim 7 wherein the instrument aperture descends into the second receiving block surface along an axis oriented at least substantially parallel to the first receiving block surface.

9. The instrument holder of claim 1 wherein one or more surfaces of the receiving block each includes intersecting valleys formed therein.

10. The instrument holder of claim 9 wherein the placement of:
- a. the intersecting valleys in the receiving block, and
- b. the prongs of the base block, are the same, whereby the intersecting valleys can receive the prongs therein when the receiving block is urged onto the prongs.

11. The instrument holder of claim 1 wherein the receiving block is penetrated by:
- a. the prongs, and
- b. one or more of:
  - (1) a hypodermic syringe cap,
  - (2) a hypodermic syringe, and
  - (3) a scalpel.

12. An instrument holder including:

a. a base block having:

(1) an upper base block surface having at least two elongated prongs extending therefrom, the prongs having at least approximately parallel lengthwise axes, (2) an opposing lower base block surface having mounting means thereon or therein for removably and inviolably mounting the lower surface to a placement surface, b. a receiving block:

(1) formed of material which is resiliently expandable, (2) having:

(a) a first receiving block surface including at least two prong apertures formed therein, each prong aperture being situated to receive a respective one of the prongs when the first receiving block surface is urged onto the prongs, and (b) a second receiving block surface including an instrument aperture formed therein, wherein each prong has a length of at least one-third of a height of the receiving block, whereby the prongs extend at least one-third of the way through the receiving block when the receiving block is urged onto the prongs.

13. The instrument holder of claim 12 wherein the mounting means includes one or more of:

a. a magnet on or within the lower base block surface, b. ferromagnetic material on or within the lower base block surface, b. a suction cup on the lower base block surface, and c. a tacky surface on the lower base block surface.

14. The instrument holder of claim 12:

a. further including a mounting block having a handle defined thereon, b. wherein:

(1) one of the base block and the mounting block has magnetic material thereon or therein, and (2) the other of the base block and the mounting block has ferromagnetic material thereon or therein.

15. The instrument holder of claim 12 wherein the second receiving block surface is oriented at least substantially perpendicular to the upper base block surface.

16. An instrument holder including:

a. a base block:

(1) including an upper base block surface and an opposing lower base block surface, (2) wherein the upper base block surface has at least two elongated prongs extending therefrom, b. a mounting block:

(1) including an upper mounting block surface and an opposing lower mounting block surface, (2) wherein the upper mounting block surface and lower base block surface are magnetically attracted together, c. a receiving block formed of material which is:

(1) resiliently expandable, and (2) configured to be readily penetrated by the prongs when the receiving block is urged onto the prongs, the receiving block thereby being removably affixed to the base block.

17. The instrument holder of claim 16 wherein the lower mounting block surface includes a handle thereon.

18. The instrument holder of claim 16 wherein:

a. the receiving block includes an upper receiving block surface, an opposing lower receiving block surface, and a side receiving block surface therebetween, b. the side receiving block surface includes an instrument aperture defined therein, the instrument aperture being centrally located on the side receiving block surface, c. the lower receiving block surface includes at least two prong apertures defined therein, d. the placement of:

(1) the prong apertures in the lower receiving block surface, and (2) the prongs of the base block, are the same, whereby the prong apertures can receive the prongs therein when the receiving block is urged onto the prongs.

19. The instrument holder of claim 18 having one or more of the following features:

a. the instrument aperture is defined at the intersection of two valleys defined within the side receiving block surface, b. at least one of the prong apertures is defined at the intersection of two valleys defined within the lower receiving block surface.

20. The instrument holder of claim 1 wherein each prong has a length of at least one-third of a height of the receiving block, whereby the prongs extend at least one-third of the way through the receiving block when the receiving block is urged onto the prongs.

* * * * *